United States Patent [19]

Jackman et al.

[11] Patent Number: 4,940,815

[45] Date of Patent: Jul. 10, 1990

[54] PROCESS FOR THE PRODUCTION OF THIOCARBOHYDRAZIDE

[75] Inventors: Dennis E. Jackman, Prairie Village, Kans.; Gary W. Combs, Blue Springs, Mo.; Dietmar B. Westphal, Remscheid, Fed. Rep. of Germany

[73] Assignee: Mobay Corporation, Pittsburgh, Pa.

[21] Appl. No.: 324,842

[22] Filed: Mar. 17, 1989

[51] Int. Cl.$^5$ ............................................. C07C 337/06
[52] U.S. Cl. ...................................................... 564/18
[58] Field of Search ............................... 564/18; 562/28

[56] References Cited

U.S. PATENT DOCUMENTS

| | | | |
|---|---|---|---|
| 2,726,263 | 12/1955 | Audrieth et al. | 260/552 |
| 3,198,698 | 8/1965 | Reuter et al. | 167/22 |
| 4,172,092 | 10/1979 | Malone | 260/552 SC |
| 4,294,985 | 10/1981 | Cramm et al. | 564/18 |

*Primary Examiner*—Richard L. Raymond
*Assistant Examiner*—P. O'Sullivan
*Attorney, Agent, or Firm*—Joseph C. Gil; Lyndanne M. Whalen

[57] ABSTRACT

TCH is produced in two stages. In the first stage, carbon disulfide and excess hydrazine are reacted in the presence of a mercaptan and optionally a strong base or an amine other than hydrazine. Carbon disulfide and a strong base (if none was present during the first stage) are then added to the reaction mixture which is further reacted to complete the formation of TCH.

10 Claims, No Drawings

PROCESS FOR THE PRODUCTION OF THIOCARBOHYDRAZIDE

BACKGROUND OF THE INVENTION

The present invention relates to an improved process for the production of thiocarbohydrazide.

Several processes for the manufacture of thiocarbohydrazide (TCH) are known. TCH may be obtained in moderate yields during the hydrazinolysis of thiophosgene in an ether or water reaction medium. It is also known to manufacture TCH by hydrazinolysis of diethylxanthate and by heating the two reaction components in the absence of a solvent. Yields of 70-74% of theory may be obtained by the latter process.

It is also known to prepare thiocarbohydrazide through conversion of dialkyltrithiocarbonates with hydrazine. Cyclic trithiocarbonate may also be used for this synthesis.

The most common synthesis of thiocarbohydrazide is, however, the conversion of carbon disulfide with hydrazine. Hydrazinium-dithiocarbazinate forms according to equation (1):

$$CS_2 + 2H_2NNH_2 \rightarrow H_2NNHCSSH.NH_2NH_2 \quad (1)$$

This compound is then converted to thiocarbohydrazide with evolution of hydrogen sulfide according to equation (2):

$$H_2NNHCSSH.NH_2NH_2 \rightarrow H_2NNHCSNHNH_2 + H_2S \quad (2).$$

Better yields and pure product may be obtained when the hot aqueous solution of the hydrazinium-dithiocarbazinate is digested with lead oxide (Stolle, et al., Ber. 41, 1099 (1908)). The yields of thiocarbohydrazide can also be increased when conducting the decomposition of hydrazinium-dithiocarbazinate in aqueous solution in the presence of hydrazine (U.S. Patent No. 2,726,263). However, increasing dilution of the hydrazine-containing reaction medium with water decreases the yield of TCH. Further, use of a water-free solvent for hydrazine (e.g., methyl, ethyl, or propyl alcohol) does not increase the TCH yield.

In each of the above-described processes, any excess hydrazine must be recovered. Such recovery is costly, time consuming and troublesome due to the reactivity and instability of hydrazine.

U.S. Pat. No. 4,294,985 teaches that the mother liquor containing the excess hydrazine may be recycled instead of being recovered. However, recycling of the hydrazine-containing liquor creates new problems. More specifically, recycling results in the build up of impurities which can reduce the yield of TCH. Further, some of the hydrazine containing liquor must be purged from the system after each recycle resulting in loss of hydrazine.

It is also known to convert hydrazinium dithiocarbazinate to TCH thermally. Yields of approximately 70% may be obtained by such thermal conversion processes.

Production of TCH by pyrolyzing a reaction mixture containing carbon disulfide and hydrazine hydrate is also known. The yields of such processes are detrimentally affected by side reactions which result in the formation of ammonia and sulfur. These side reactions are further catalyzed by the sulfur formed.

It would therefore be advantageous to develop a process for producing TCH (1) which did not require removal or recycling of excess of hydrazine, (2) which suppressed side reactions resulting in the formation of ammonia and sulfur and (3) which produced TCH in high yield.

SUMMARY OF THE INVENTION

It is an object of the present invention to provide an improved process for producing TCH in high yield in which removal or recycling of excess hydrazine is not required and in which formation of ammonia and sulfur by-products is suppressed.

It is also an object of the present invention to provide an improved process for producing TCH in which the mother liquor recovered from the reaction mixture is treated to react the excess hydrazine present therein to form TCH.

It is a further object of the present invention to provide catalysts for a process for producing TCH in high yield which are inexpensive enough to discard or more stable and more easily recovered than hydrazine.

These and other objects which will be apparent to those skilled in the art are accomplished by reacting carbon disulfide and excess hydrazine in the presence of a mercaptan and optionally a strong base or an amine other than hydrazine, cooling the reaction mixture, adding carbon disulfide and if not present during the first reaction, a strong base or an amine (other than hydrazine) in amounts sufficient to react with any hydrazine present and pyrolyzing the mixture to form TCH.

DETAILED DESCRIPTION OF THE INVENTION

In the process of the present invention, carbon disulfide and hydrazine are reacted in the presence of a mercaptan and optionally a strong base or an amine (other than hydrazine). Carbon disulfide and if not present during the first reaction, a strong base or an amine other than hydrazine are then added to the reaction mixture (usually after the reaction mixture has been cooled) in sufficient quantity to react with the hydrazine remaining in the mixture. Strong base or amine may, of course, be added prior to the second reaction even though such base or amine was present during the first reaction. The mixture is again heated to complete the formation of TCH.

The reaction of carbon disulfide with excess hydrazine in the presence of a mercaptan is generally carried out at a temperature of from 60° to 80° C. for 6-10 hours. This reaction may be summarized by the following equation:

$$CS_2 + \underset{\text{excess}}{NH_2NH_2.H_2O} + RSH \longrightarrow \quad (I)$$

$$TCH + H_2S + NH_2NH_2 + HDTC$$

The initial product of carbon disulfide and hydrazine is hydrazinium dithiocarbazinate (HDTC), a water soluble salt formed in nearly quantitative yield at relatively low temperatures (e.g. 20° C.). When the HDTC is heated (e.g. at a temperature of from 50° to 85° C.) in the presence of excess hydrazine, $H_2S$ is given off and TCH forms.

Carbon disulfide and a strong base or an amine other than hydrazine are then added to the reaction mixture (if not already present), usually after that reaction mixture has been cooled. Carbon disulfide is added in an amount sufficient to react with the hydrazine present. The resultant mixture is then heated to a temperature of from about 60° to 80° C. for 16-24 hours. The reactions which occur may be represented by the following equations:

$$NH_2NH_2 \, H_2O + MX + H_2NNHCSS^\ominus \, H_3\overset{\oplus}{N}NH_2 \longrightarrow \quad (II)$$
$$(MDTC)$$

$$H_2NNHC\overset{S}{\underset{\|}{C}}S^\ominus M^\oplus + H_2NNH_2 + HX$$

$$MDTC + NH_2NH_2 \longrightarrow TCH + MSH \cdot \quad (III)$$

$$MSH + HDTC \longrightarrow MDTC + H_2S + NH_2NH_2 \quad (IV)$$

in which MX represents the strong base or amine with M representing the cation and X representing the anion.

The TCH is recovered (e.g. by filtration) and may be washed with an appropriate material such as water and/or an alcohol such as methanol. The mother liquor may then be discarded.

Where no mercaptan is present in the reaction mixture during the reaction represented by equation I, the recovered HDTC contains sulfur. When this HDTC-containing sulfur is further reacted with hydrazine, TCH and by-products such as

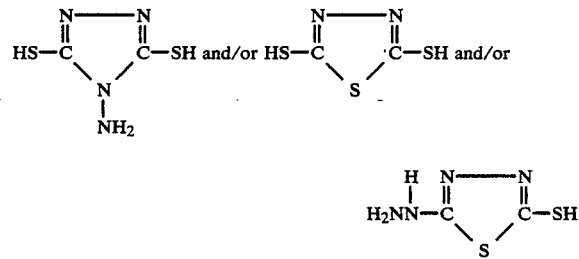

are formed. The yield of TCH is substantially reduced due to formation of these by-products.

However, the inclusion of a mercaptan in the reaction mixture in accordance with the present invention eliminates the formation of these unwanted by-products. It is believed that the mercaptan intercepts any sulfur as it slowly forms from $H_2S$ and hydrazine. Consequently, the HDTC formed can be used without experiencing the reduction in TCH yield due to by-product formation.

In the reaction of carbon disulfide with hydrazine in accordance with the present invention, the hydrazine may be employed in the form of hydrazine hydrate or as an aqueous hydrazine hydrate. It is possible to use a commercial grade of hydrazine hydrate. One may even use an 80 to 85% product. It is not necessary to use a completely pure hydrazine hydrate. It should be noted that the phrase "hydrazine hydrate" is used herein to identify hydrazine combined with one molecule of water as represented by the formula:

$$NH_2NH_2.H_2O \text{ or } N_2H_5OH.$$

The water content of the hydrazine hydrate should preferably not exceed 40% by weight, because above this limit the yield gradually decreases with an increasing water content. For economical reasons, it is preferable to carry out the process of the invention with an aqueous hydrazine hydrate having a water content of up to about 40% by weight.

The hydrazine hydrate is generally used in the process of the present invention in excess of the stoichiometric amount, preferably in an amount of from two to four times the molar amount of carbon disulfide initially present, most preferably between two and three times the molar amount of carbon disulfide. The use of a greater excess of hydrazine hydrate is of no particular advantage and is therefore avoided for economic reasons.

Any mercaptan or thiol (i.e. organic compound resembling an alcohol but having the oxygen of the hydroxyl groups replaced by sulfur) or compound which forms a mercaptan or thiol under the reaction conditions may be used in the process of the present invention. Mercaptoethanol, thioglycolic acid, ethane dithiol and other water soluble mercaptans having a high boiling point (i.e. a boiling point greater than about 80° C.) are particularly preferred mercaptans. Examples of compounds which form mercaptans under the reaction conditions include ethylene dichloride, 2-chloroethanol and propylene oxide. The mercaptan or mercaptan-forming compound is generally used in a quantity of up to about 5 mole %, preferably from 1.5 to 5 mole % and most preferably from 2.5 to 3.5 mole %. These quantities are reduced by 50% where a dithiol is used because the dithiol provides two SH groups per molecule.

The strong base which may optionally be present during the first reaction which occurs in the process of the present invention may be an amine other than hydrazine or a strong base, preferably an inorganic base. The amine base used in the process of the present invention may be any compound having a $pK_b$ value of from 3 to 6 (preferably from 3 to 4) other than hydrazine. Examples of such bases include aliphatic amines such as triethylamine, tetramethylethylenediamine, ammonia and diazabicylooctane. The strong bases which may be used in the process of the present invention include the hydroxides of the alkali metals such as sodium hydroxide and potassium hydroxide. Sodium hydroxide and tetramethylenediamine are particularly preferred.

When present during the first reaction, the strong base or amine may be used in an amount of up to 17 mole %.

The reaction represented by equation I may be conducted at a temperature of from about 60° to 80° C., preferably about 70° C. from about 6 to 10 hours, preferably about 8 hours.

In the second reaction of the present invention (represented by equations II, III and IV), carbon disulfide is added in an amount which is at least stoichiometrically equivalent to any hydrazine present, preferably in an amount of from 20-40 mole % of total $CS_2$ used, most preferably about 25-30 mole %.

The mercaptan may optionally be added to the reaction mixture after the first reaction has been completed in an amount of up to 50% of total mercaptan to be used. If mercaptan is added, it is preferred to add up to about 4 grams per mole of carbon disulfide added.

If no strong base or amine (selected from those described above) is present during the first stage of the reaction, the base or amine is generally added before the second stage is begun in a quantity of up to 1 mole for every mole of carbon disulfide being added after the first step, preferably from 0.5 to 1 mole strong base or amine per mole of carbon disulfide added. Less base may be added during or prior to the second reaction of the process where base was present during the first reaction.

This second reaction is generally conducted at a temperature of from about 60° to 80° C., preferably about 70° C. for from about 16 to 24 hours, preferably about 20 hours.

Upon completion of the second reaction, the reaction mixture is cooled and filtered to recover the precipitated TCH. The mother liquor may be discarded. The TCH is then washed and dried. Yields of from about 88–90% of theoretical are typically obtained by this process.

In addition to good yields of TCH formed without generation of sulfur and ammonia, the present invention is advantageous because it may be carried out in a single reactor with relatively inexpensive equipment.

Having thus described our invention, the following Examples are given to illustrate this invention.

EXAMPLES

EXAMPLE 1

To a 15° C. stirred mixture of 6 moles of hydrazine hydrate (300 gm) and 5.0 gm of mercaptoethanol were added 2.16 moles of carbon disulfide (164 gm) dropwise so that the temperature did not rise above 40° C. (1–2 hrs). The mixture was then heated at 70° C. for 8 hrs while trapping the $H_2S$ off-gas in a caustic scrubber. The mixture was then cooled to 20° C. and 0.75 mole of 50% NaOH (64 gm) and 0.84 mole of carbon disulfide (64 gm) were added simultaneously while the temperature was kept below 40° C. The mixture then underwent a second 70° C. cook for about 20 hrs, was cooled to below 50° C., and the TCH was filtered, washed with water, and air dried. The TCH yield was about 283 gm (89%).

EXAMPLES 2–12

The procedure of Example 1 was repeated using the same materials in the quantities indicated in Table 1 for the reaction times and at the reaction temperatures indicated in Table 1 to obtain TCH in the yields reported in Table 1.

TABLE 1

| No. | Step | HyHy Mole | CS$_2$ Mole | NaOH Mole | ME gm | H$_2$O gm | Temp °C. | Time (hrs) | TCH gm | TCH A.I. | TCH N.Y. |
|---|---|---|---|---|---|---|---|---|---|---|---|
| 2* | (a) | 6 | 2 | .5 | 0 | 20 | 68 | 8 | | | |
|    | (b) | 0 | 1 | 0 | 0 | 0 | 76 | 16 | 279.0 | 99.9 | 87.7 |
| 3* | (a) | 6 | 2 | .5 | 0 | 20 | 68 | 8 | | | |
|    | (b) | 0 | 1.06 | 0 | 0 | 0 | 75 | 16 | 279.2 | 97.8 | 85.9 |
| 4  | (a) | 6 | 2.5 | .5 | 15 | 20 | 73 | 3 | | | |
|    | (b) | 0 | .5 | 0 | 0 | 0 | 70 | 20 | 274.8 | 99.2 | 85.7 |
| 5  | (a) | 6 | 2.5 | .5 | 0 | 20 | 73 | 3 | | | |
|    | (b) | 0 | .5 | 0 | 0 | 0 | 70 | 20 | 270.1 | 100 | 84.9 |
| 6  | (a) | 6 | 2 | 0 | 0 | 0 | 65 | 16 | | | |
|    | (b) | 0 | 1 | 1 | 0 | 40 | 65 | 16 | 285.5 | 98.8 | 88.7 |
| 7  | (a) | 6 | 2 | .5 | 5 | 20 | 70 | 4 | | | |
|    | (b) | 0 | 1 | 0 | 0 | 0 | 70 | 19 | 274.3 | 99.1 | 85.5 |
| 8* | (a) | 6 | 2 | .5 | 0 | 20 | 68 | 8 | | | |
|    | (b) | 0 | 1 | 0 | 0 | 0 | 72 | 16 | 287 | 98.9 | 89.3 |
| 9  | (a) | 6 | 2 | 1 | 10 | 40 | 72 | 18 | | | |
|    | (b) | 0 | 1.06 | 0 | 3 | 0 | 72 | 21 | 282 | 100 | 89.0 |
| 10 | (a) | 6 | 2 | 0 | 5 | 0 | 72 | 5 | | | |
|    | (b) | 0 | 1 | .5 | 0 | 20 | 72 | 20 | 281 | 99.0 | 87.5 |
| 11 | (a) | .6 | 2.5 | .5 | 5 | 20 | 65 | 12 | | | |
|    | (b) | 0 | 0.5 | 0 | 0 | 0 | 72 | 16 | 285.8 | 100 | 89.9 |
| 12 | (a) | 6 | 2.5 | 0 | 5 | 0 | 65 | 12 | | | |
|    | (b) | 0 | 0.5 | .5 | 0 | 20 | 72 | 16 | 285.6 | 100 | 89.9 |

*Used 7.5 gm EdCl as anti-oxidant
HyHy = hydrazine hydrate
ME = mercaptoethanol
A.I. = active ingredient
N.Y. = Net yield Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of TCH comprising
   (a) reacting carbon disulfide and excess hydrazine in the presence of a mercaptan and optionally a strong base or an amine other than hydrazine to form TCH,
   (b) adding carbon disulfide in an amount which is at least sufficient to react with any unreacted hydrazine present and a strong base or an amine other than hydrazine to the reaction mixture of (a) if a strong base or an amine other than hydrazine was not present during (a) and
   (c) heating the mixture of (b) to form TCH.

2. The process of claim 1 in which the mercaptan is mercaptoethanol.

3. The process of claim 2 in which the strong base is sodium hydroxide.

4. The process of claim 1 in which the strong base is sodium hydroxide.

5. The process of claim 1 in which strong base is present during the reaction of step (a).

6. The process of claim 5 in which strong base is added in (b).

7. The process of claim 1 in which the carbon disulfide added in step (b) is added in a quantity which is about 25–30 mole % of total carbon disulfide used in the process.

8. The process of claim 1 in which the reaction of step (a) is carried out at a temperature of from about 60° to 80° C. for about 6 to 10 hours.

9. The process of claim 7 in which the reaction of step (b) is carried out at about 60° to 80° C. for about 16–24 hours.

10. The process of claim 1 in which the mercaptan is used in a quantity of from 1.5 to 5 mole %.

* * * * *